(12) United States Patent
Sharma

(10) Patent No.: US 7,470,544 B2
(45) Date of Patent: Dec. 30, 2008

(54) SENSOR ARRAY USING SAIL

(75) Inventor: Manish Sharma, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 467 days.

(21) Appl. No.: 11/138,619

(22) Filed: May 26, 2005

(65) Prior Publication Data

US 2006/0270057 A1    Nov. 30, 2006

(51) Int. Cl.
G03F 7/00 (2006.01)
H01B 13/00 (2006.01)
C03C 15/00 (2006.01)
G01R 31/00 (2006.01)
G01N 1/00 (2006.01)

(52) U.S. Cl. .......................... 436/174; 430/320; 216/16; 216/41; 216/59

(58) Field of Classification Search .................... 8/480; 436/174; 430/320; 216/16, 41, 59
See application file for complete search history.

(56) References Cited

U.S. PATENT DOCUMENTS

| | | | |
|---|---|---|---|
| 5,256,247 A * | 10/1993 | Watanabe et al. ............. | 216/16 |
| 5,260,175 A * | 11/1993 | Kowanz et al. .............. | 430/326 |
| 5,512,131 A | 4/1996 | Kumar et al. | |
| 5,719,033 A | 2/1998 | Ackley et al. | |
| 6,348,999 B1 * | 2/2002 | Summersgill et al. ....... | 359/569 |
| 6,377,721 B1 | 4/2002 | Walt | |
| 6,464,942 B2 | 10/2002 | Coffman et al. | |
| 6,517,995 B1 * | 2/2003 | Jacobson et al. ............. | 430/320 |
| 6,667,159 B1 | 12/2003 | Walt et al. | |
| 6,682,649 B1 | 1/2004 | Petersen et al. | |
| 6,699,665 B1 | 3/2004 | Kim et al. | |
| 6,856,161 B2 | 2/2005 | Thewes | |
| 6,872,522 B1 | 3/2005 | Mecklenburg et al. | |
| 2002/0105080 A1 * | 8/2002 | Speakman ................... | 257/749 |
| 2004/0002216 A1 | 1/2004 | Taussig et al. | |
| 2004/0097072 A1 * | 5/2004 | Carter et al. ................. | 438/678 |
| 2004/0219074 A1 | 11/2004 | Childers et al. | |
| 2005/0121378 A1 * | 6/2005 | Yamazaki et al. ......... | 210/198.2 |
| 2006/0063387 A1 * | 3/2006 | Miller et al. ................. | 438/735 |

OTHER PUBLICATIONS

Gale, B.K., Caldwell, K.D., Frazier, A.B. "Electrical conductivity particle detector for use in biological and chemical micro-analysis systems" Sep.1998, pp. 1-12.

* cited by examiner

Primary Examiner—Jill Warden
Assistant Examiner—Lore Ramillano

(57) ABSTRACT

Provided is a sensor array and a method of forming the same. The sensor array includes an array of apertures etched into a 3D patterned resist layer to expose areas of one or more agents and/or reagents deposited on a substrate. The sensor is formed using a Self-Aligned Imprint Lithography ("SAIL") method, a process that allows for a one-time deposition of all required materials followed by a series of etching/cleaning steps. The location of reagents on the sensor template, as well as the concentration gradient of each reagent, may be controlled through the sensor manufacturing process. Bores of a single reagent, or bores containing two or more reagents, may be formed using the SAIL process.

16 Claims, 6 Drawing Sheets

SENSOR ARRAY USING SAIL

FIELD OF THE INVENTION

The present invention relates generally to the field of forming sensor devices for testing, and in particular to an improved sensor for agent-reagent testing.

BACKGROUND

Advances in medicine and science often include advances in the test hardware and techniques used to analyze materials and validate theories. In the biotech industry, there is an increasing need to determine the response of a given bacteria to pharmaceutical agents by reacting the bacteria with one or more antibiotics in a quick and efficient manner. In support of this need, the development of biotech hardware for testing continues at a rapid pace. When designing hardware and procedures for testing, there is a constant struggle between maintaining sterile conditions, accurately controlling test variables, and testing on a larger, more cost efficient scale.

The testing of various chemicals or agents, such as biological antigen-antibody pairs, often requires the manufacture and use of a test template having a plurality of agent or reagent containing cells. In some instances reagents are deposited into separate cells, after which a test material potentially containing one or more agents of interest is introduced into the cells. The interaction between agents and reagents can be observed (optically or otherwise) to determine if a certain agent is present in the test material. Often times, the concentration level of the agent present in the test material can be determined as well.

Typically, very small quantities of materials (e.g. agents and reagents) are used in the tests described above. The test templates or structures used to house the agents/reagents may be relatively small as well. Manufacturing techniques such as imprint lithography and photolithography can be used to manufacture test templates having very precise dimensions on the order of a few nano-meters (nms). These manufacturing techniques, however, can be very expensive to implement, and the challenges associated with alignment of components, repeatability and large scale manufacturing, etc. can be significant.

Frequently, quality control measures discard an unacceptable percentage of templates before they reach the test environment, or during the course of testing. As such, templates for chemical/biological testing are generally more expensive than they otherwise might be, as the manufacturers must recoup the costs for resources, time and precise tooling for the acceptable templates as well as the unacceptable templates. Also, given the fact that in most instances test templates for chemical/biological testing are a "one-time" use product, the costs per test can be very high.

In addition to the problems associated with the manufacture and use of test templates meeting strict test parameters for size, sterility, etc., current methods of chemical/biological testing are limited by the manner in which test materials are dispensed/distributed within a test template. For example, the precise placement of sample agents and/or reagents in the cells of a test template can be a time consuming, difficult task. Various techniques known in the art for the deposition of materials either lack the precision desired, or they are prohibitively complex and expensive to implement. This is especially true when multiple agents or reagents are deposited into a single test template in varying patterns. Even more complex is the challenge of placing two or more agents/reagents into a single cell.

Hence, there is a need for a process to provide a sensor template for chemical/biological testing that overcomes one or more of the drawbacks identified above.

SUMMARY

The present disclosure advances the art by providing a method of forming a sensor array.

In particular and by way of example only, according to an embodiment, provided is a method of forming a sensor array including: providing a substrate; disposing one or more reagents upon the substrate; depositing at least one resist layer over the one or more reagents; establishing a three-dimensional structure in the resist layer; and etching the three-dimensional structure to expose the one or more reagents.

DETAILED DESCRIPTION

Figure 1:
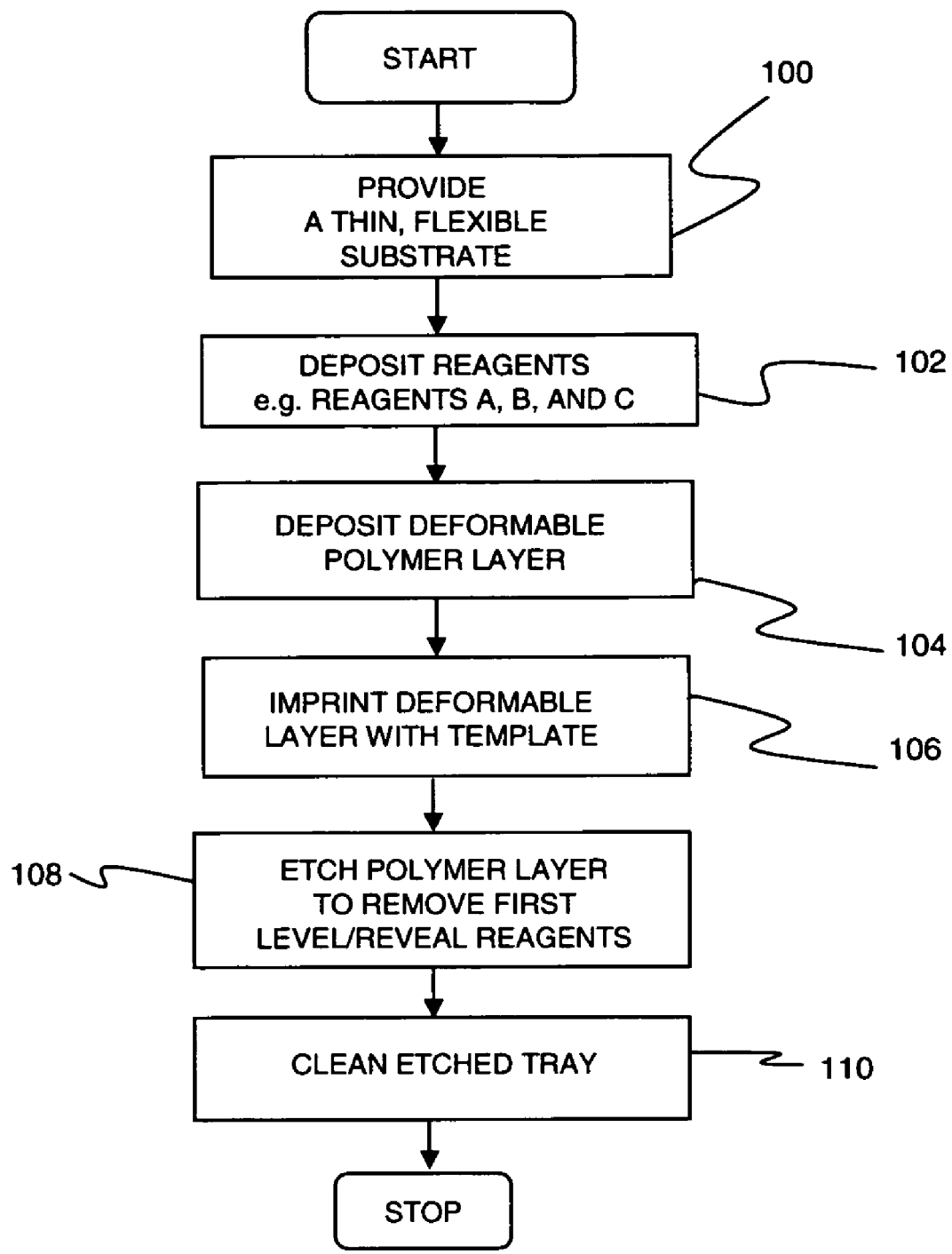
FIG. 1 is a flowchart of a method for forming a sensor array, according to an embodiment.

Before proceeding with the detailed description, it is to be appreciated that the present teaching is by way of example, not by limitation. Thus, although the instrumentalities described herein are for the convenience of explanation shown and described with respect to exemplary embodiments, it will be appreciated that the principles herein may be equally applied in other types of sensor arrays.

In at least one embodiment, the method for forming a sensor array incorporates Self-Aligned Imprint Lithography ("SAIL"), a recently developed technique for producing multilayer patterns on flexible substrates. The basics of this process are set forth and described in U.S. patent application Ser. No. 10/184,567, US Patent Publication Number 04-0002216, now U.S. Pat. No. 6,861,365, the disclosure of which is incorporated herein by reference.

The SAIL technique uses a 3D patterned resist layer and is typically employed in roll-to-roll processing. As the 3D patterned resist layer is flexible, disposed upon and more specifically joined to the substrate or underlying material layers during fabrication, the pattern will stretch or distort to the same degree as the substrate and intervening material layers, if provided. Such flexibility permits advantageously precise alignment for feature development. As such, a SAIL roll-to-roll fabrication process may be employed to provide low cost manufacturing solutions for devices such as flat and/or flexible displays, trays, and templates, or other devices suitable for roll-to-roll processing. It shall also be realized that the disclosed method may be employed upon a non-flexible substrate while remaining within the spirit and scope of at least one embodiment.

Referring now to the drawings, FIG. 1 through FIG. 9 conceptually illustrate at least one embodiment of a sensor array, and a method of manufacturing the same using SAIL. In at least one embodiment, the sensor array is a multiple functionality sensor. It will be appreciated that the described process need not be performed in the order in which it is herein described, but that this description is merely exemplary of one preferred method of fabricating at least one sensor.

In FIG. 1, a flowchart is provided as a visual overview of at least one embodiment for forming a sensor array. As indicated in block 100, the processes is generally commenced by providing a flexible substrate. Typically, the substrate is of a type well known in the art for use with a roll-to-roll processing technique, such as is the basis of the SAIL process. One or more reagents are then deposited upon the substrate, block 102. In at least one embodiment, the reagents are biological reagents.

Multiple columns, rows, layers or other configurations of a single reagent may be deposited. Alternatively, multiple reagents may be deposited according to a predetermined pattern which may include one or more column, row, layer or other configurations of each reagent. Collectively, the columns, rows, layers or other configurations of reagents form a sensor array used to test and/or detect various agents. In at least one embodiment the reagents may be layered, as in one or more atop another. In an alternative embodiment, the reagents are juxtaposed.

A deformable resist layer is then deposited over the one or more reagents, block 104. Preferably the resist layer is a polymer based material, however, any material well known in the art as suitable for selective etching may be used, to include both organic and inorganic materials. The resist or polymer may incorporate any of a variety of commercially available polymers. For example, a polymer from the Norland optical adhesives (NOA) family of polymers could be used. A silicone material may also be used as is described in U.S. patent application Ser. No. 10/641,213 entitled "A Silicone Elastomer Material for High-Resolution Lithography", which is herein incorporated by reference.

A method for utilizing a stamping tool to generate a 3D template in a layer of material is described in U.S. patent application Ser. No. 10/184,587 entitled "A Method and System for Forming a Semiconductor Device", which is herein incorporated by reference. A stamping tool is further described in U.S. patent application Ser. No. 10/903,300 entitled "Imprint Stamp", which is herein incorporated by reference. With further respect to roll-to-roll processing where substrate may be of arbitrary size, yet another method for providing a 3D template is described in U.S. Pat. No. 6,808,646, entitled "Method of Replicating a High Resolution Three-Dimension Imprint Pattern on a Compliant Media of Arbitrary Size", which is also herein incorporated by reference.

Generally speaking, when employing a stamp and polymer, a stamping tool is brought into contact with the polymer, thereby displacing the polymer layer into the 3D pattern provided by the stamping tool. Typically, the displaced polymer is then cured, such as by UV light exposure, or by heat or any other suitable curing means. The result is a 3D patterned resist layer having a plurality of vertical heights throughout the structure (block 106).

The one or more reagents and the 3D patterned resist layer are then etched, block 108. This etching forms the rudimentary structure for a sensor array. The rudimentary structure is transformed into at least one sensor by further etching and cleaning the 3D patterned resist layer, the underlying levels of reagents, and the substrate, block 110.

As is discussed in detail below, it is to be appreciated that under the present method, a planarizing material need not be employed. More specifically, all reagent layers are advantageously deposited before etching is performed, and subsequent planarization steps and the deposition of further material layers are not required to achieve a sensor array.

Turning now to FIGS. 2-6, provided is a simplified, graphic illustration of the initial processes described above for forming a sensor array 200. Specifically, in FIG. 2 there is shown a substrate 201. Typically, substrate 201 is chemically cleaned to remove any particulate matter, organic, ionic, and or metallic impurities or debris which may be present upon the surface of substrate 201. As discussed above, substrate 201 may be a flexible material suitable for roll-to-roll processing and subsequent processing steps. In at least one embodiment substrate 201 is, for example, a polyimide plastic sheet with or without an inorganic coating.

Figure 2:
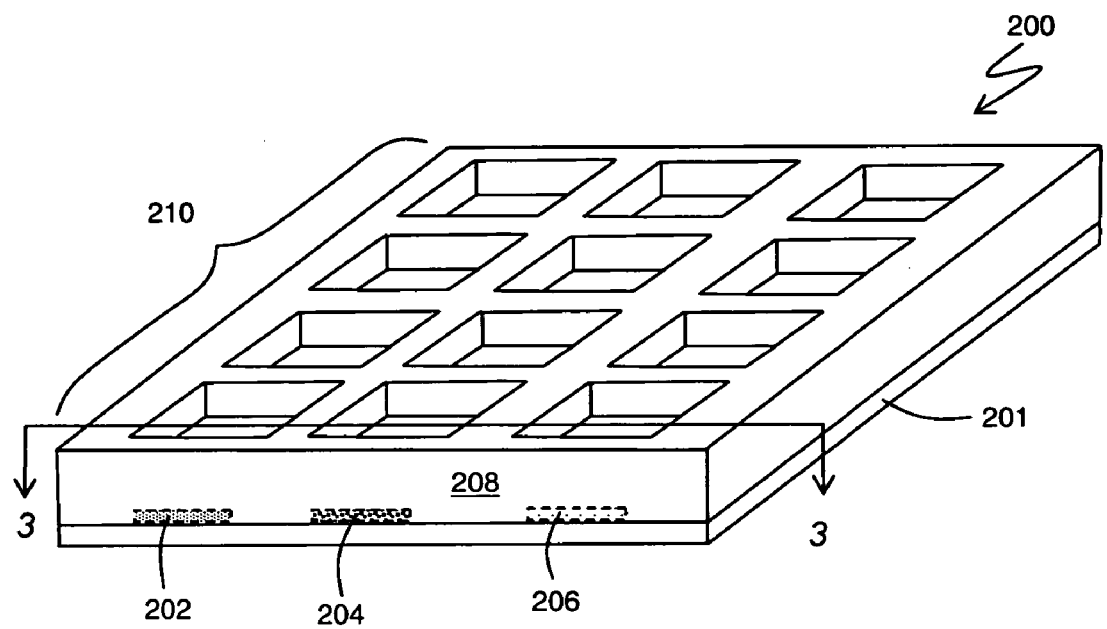
FIG. 2 is a perspective view of a sensor array having a 3D patterned resist layer prior to etching, according to an embodiment.

One or more reagents, which may be biological reagents, are deposited onto substrate 201. As shown in FIG. 2, multiple reagents 202, 204 and 206 may be deposited in a predetermined pattern. Cross-referencing for a moment FIGS. 2 and 3, it can be seen that the patterns of reagents 202-206 may vary, and may include a plurality of continuous layers of the same reagent, e.g. layer 300. Further, continuous and juxtaposed layers of differing reagents 202, 204 (e.g. layers 300 and 302) may be used.

In addition, varying patterns of reagents 202-206, as shown in layer 304, may be required or desired. The shape of the layers 300-304 of reagents 202-206 may vary as well, and may include geometric shapes such as the triangles of FIG. 3. Alternatively, non-geometric and random shapes may be used.

The patterns and shapes selected for a given array of reagents 202-206 depends on the operational need and use of sensor array 200. It can be appreciated that reagent materials used in various medical, scientific and other tests, other than biological reagents, may be used without departing from the scope of this application.

Deposition of reagent materials 202-206 may be accomplished by any of the techniques well known in the art to include spraying, vacuum deposition, etc. For example, in one embodiment, the reagent material is suspended in a solvent or water based solution. The solvent or water is removed or "driven off", and the remaining reagent material is deposited onto substrate 201. In at least one embodiment, reagent materials 202-206 are deposited with the use of an ink-jetting printing system operable to "print" specific size and shape geometric areas of reagent materials.

Figure 3:
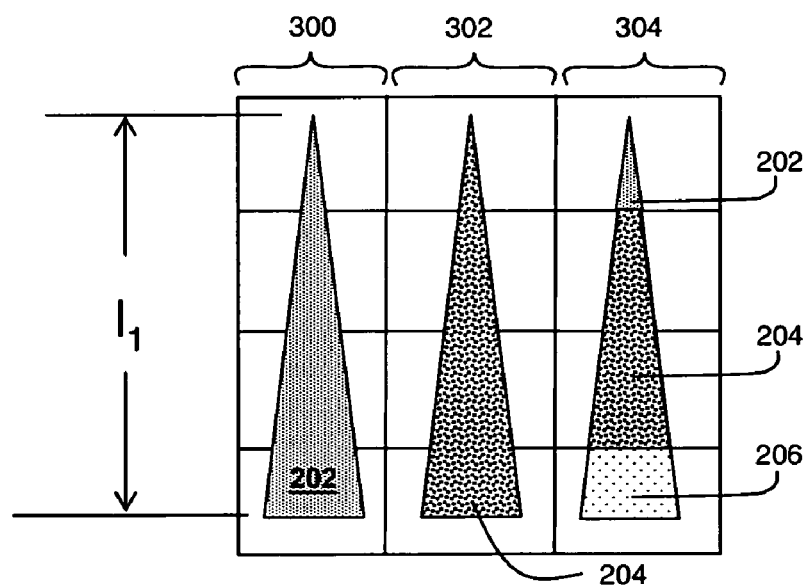
FIG. 3 is a plan view of layers of reagents, according to an embodiment.

In an alternative embodiment, the size and geometric shape of an area of deposited reagent 202-206 may be controlled, by first depositing a base material (not shown) having the desired size and shape, as well as an affinity for adhering to the selected reagent. The surface area of the base material, as well as the adhesive properties of the base material, will determine in large part the concentration or quantity of reagent material retained on substrate 201. As shown in FIG. 3, layers, e.g. layer 300, may include a concentration gradient along the length "$1_1$" of layer 300. Of note, the concentration gradient may be defined by the physical size and shape of the reagent pattern, as well as reagent thickness. In an alternate embodiment, the size, geometric shape and concentration of deposited reagent may be defined by the physical dimensions of the area on the substrate 201 onto which reagents 202-206 are deposited.

Figure 4:
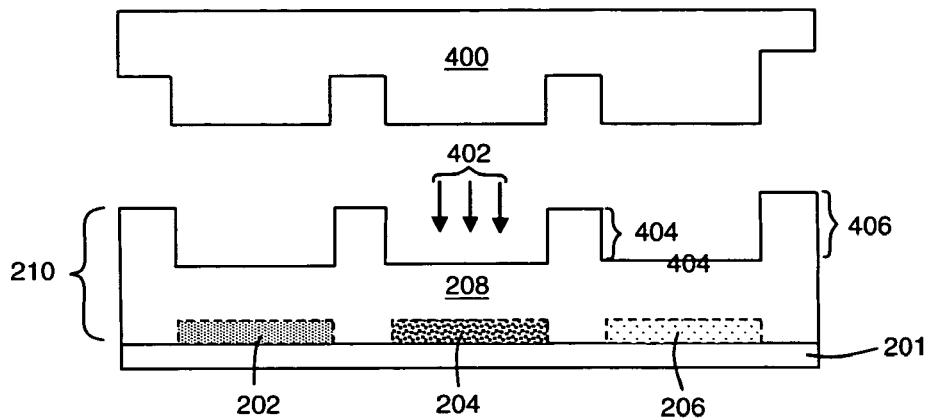
FIG. 4. is a side view of an embossing tool and imprinted 3D patterned resist, according to an embodiment.

To provide a template for etching and forming at least one sensor array 200, it is desirable to have a 3D patterned resist layer over the deposited reagent materials 202-206. In at least one embodiment, a polymer resist layer 208, such as an imprint polymer, is deposited upon the reagent materials 202-206 and imprinted by a stamping template 400 (FIG. 4). To form the desired array of reagents or chemical/biological "sensors" of sensor array 200, stamping template 400 may have an imprinting pattern with varying vertical elevations or heights—depending on the ultimate design of the sensor.

Cross-referencing FIGS. 2 and 4, a 3D stamping template or tool 400 is brought into intimate contact with polymer 208 (as illustrated by arrows 402) with sufficient force to imprint polymer resist layer 208 and establish a 3D patterned resist layer 210. Stamping template 400 may be translucent such that the stamped polymer may be hardened or otherwise cured, such as by UV light, to retain the 3D structure. In at least one embodiment, stamping template 400 may be an embossing roller such as is suitable for use in roll-to-roll processing. FIGS. 2 and 4 illustrate the resulting 3D pattern resist layer 210 having a plurality of different levels, also know as vertical heights, e.g. vertical heights 404 and 406.

Figure 5:
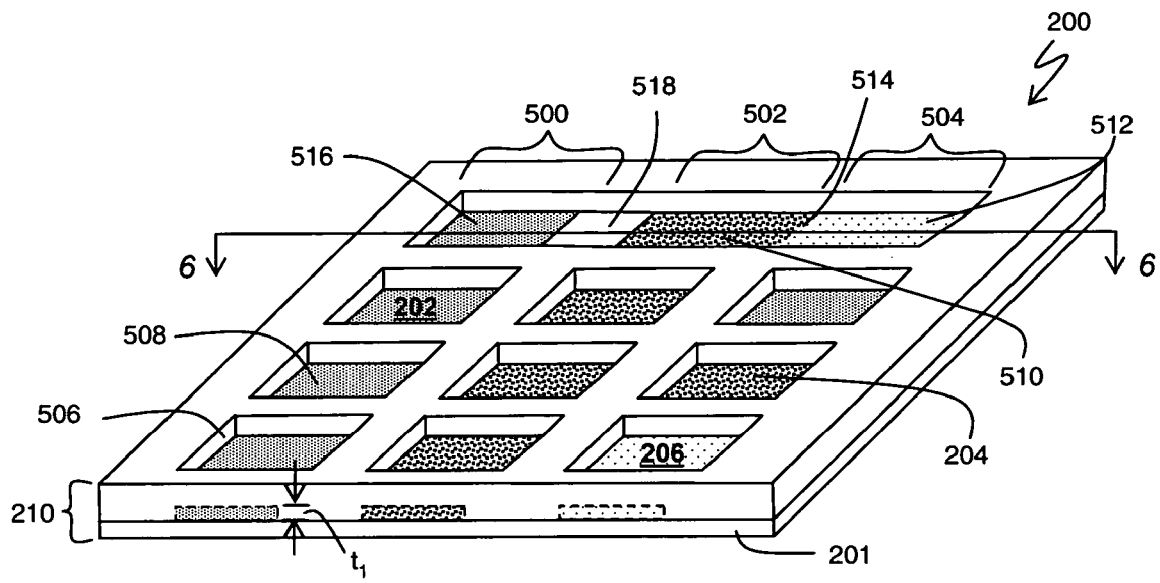
FIG. 5. is a perspective view of a sensor array, according to an embodiment.
Figure 6:
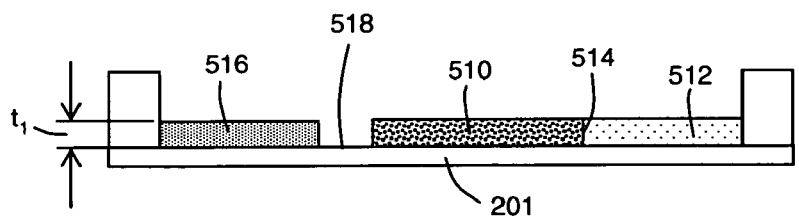
FIG. 6 is a cut-away side view of the sensor in FIG. 5, according to an embodiment.

Continuing with the example of forming sensor array 200, FIGS. 5 and 6 illustrate the results of an etching process, which may be ion etching. This etching process may involve a series of etches, first to predetermined regions of 3D patterned resist layer 210, then potentially to one or more areas of reagent materials 202-206. Preferably, in at least one embodiment the etches are substantially anisotropic. In addition, these etches may be mutually selective, which is to say a first material is etched and removed while a second material is left unaffected.

It is generally understood that an ion etching process may be accomplished by either of two traditional processes—a physical process or an assisted physical process. In a physical etching environment, no chemical agent is provided. Rather, the removal of material is entirely dependent upon the physical impact of the ions knocking atoms off the material surface by physical force alone. Physical ion etching is commonly referred to as ion milling or ion beam etching. Physical ion etching is also typically referred to as a dry process. A physical etching process is typically very anisotropic.

In an assisted physical process such as a reactive ion etching process, or RIE, removal of material comes as a combined result of chemical reactions and physical impact. Generally, the ions are accelerated by a voltage applied in a vacuum. The effect of their impact is aided by the introduction of a chemical which reacts with the surface being etched. The reaction makes the surface softer and, as such, increases both the relative control of the etching as well as the etching rate. RIE is typically also referred to as a wet etching process. The chemical reaction is also typically very isotropic.

An RIE process advantageously permits very accurate etching of the one or more layers with little appreciable affect upon other layers. In other words, specific selection of different materials permits an RIE process to soften one layer without significantly softening another.

In at least one embodiment, the removal or etching of the 3D patterned resist layer 210 is accomplished with RIE. Although ion etching and RIE have been described in conjunction with at least one embodiment, it is understood and appreciated that one of ordinary skill in the art will recognize that a variety of different etch processes could be utilized without departing from the scope and spirit herein disclosed.

As a result of etching, areas of reagent materials 202-206, such as those contained in columns 500, 502 and 504, are exposed through apertures in the 3D patterned resist layer 210, of which aperture 506 is exemplary. The reagents 202-206 have a known thickness "$t_1$" which may be a controlled variable depending on the nature of the test(s) conducted. As shown in FIG. 5, apertures (e.g. aperture 506) may be separated by additional resist material. Similarly, reagents 202-206 may be separated in one or more directions by resist or substrate material, as shown in FIG. 6.

In at least one embodiment, reagents 202-206 may be unconstrained in one or more lateral directions, and may contact one another at one or more locations. More particularly, in FIGS. 5 and 6, an area 510 of reagent 204 is in contact with an area 512 of reagent 206 along an interface 514. In yet another embodiment, all of 3D patterned resist 210 between two or more areas of reagents, e.g. areas 510 and 516, may be removed, however, the reagent pattern may be such that reagents 202, 204 are not in contact. In this instance, an exposed portion 518 of substrate 201 is located between the areas 510, 516 of reagents 202, 204.

Although illustrated with respect to a sensor array 200 having three columns 500-504 constituting an array of reagents 202-206, it will be understood and appreciated that the above described processes may be performed substantially simultaneously across a large substrate to provide either a plurality of multiple functionality sensors, or a single multiple functionality sensor having a large array of reagents, each of which act as individual "sensors" during testing.

Figure 7:
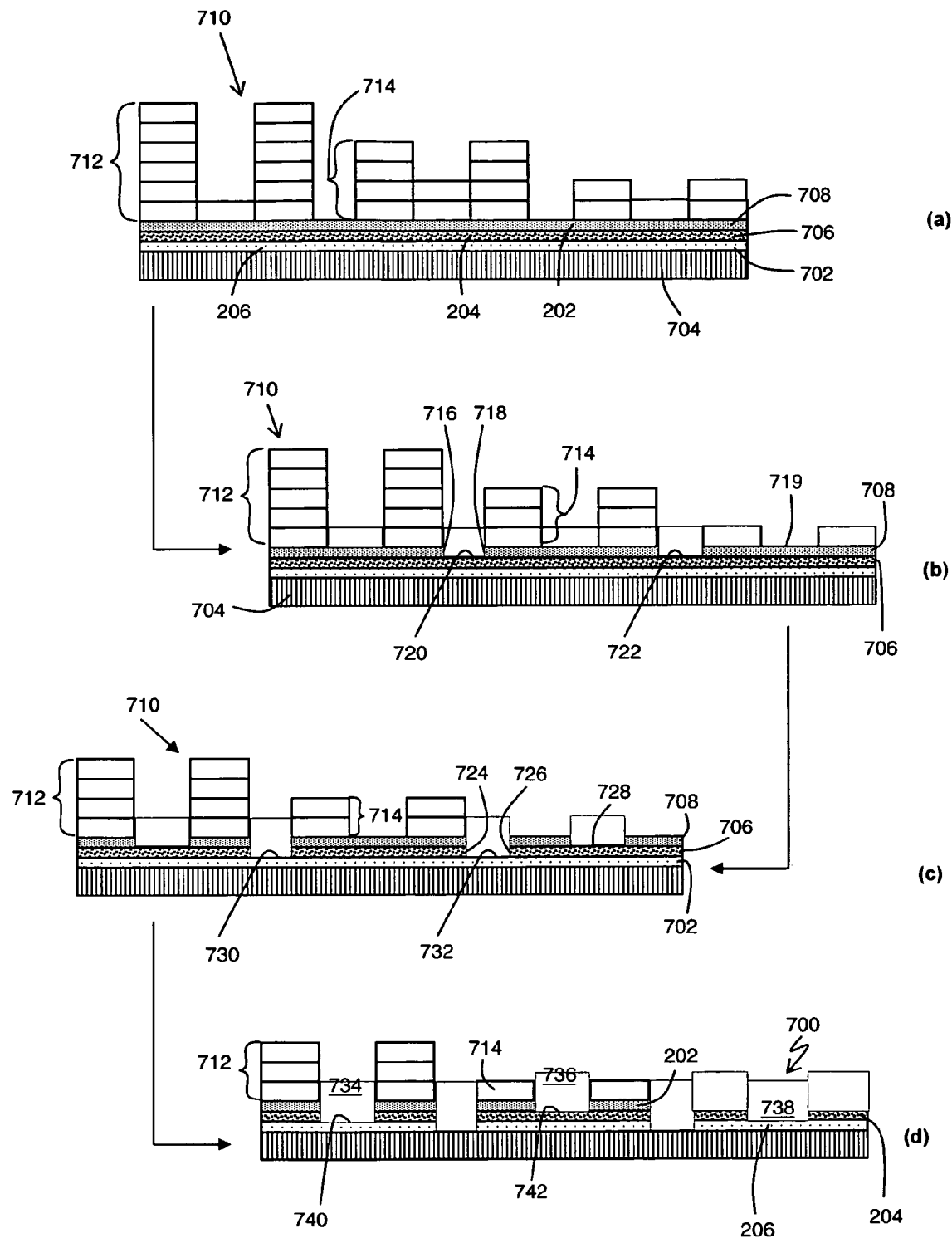
FIG. 7 is a series of side views depicting the forming of a sensor array, according to an embodiment.

Referring now to FIG. 7, the sequential development of a sensor array 700 is depicted, wherein reagents 202-206 are deposited atop one another. As shown in FIG. 7(a), a template for etching has been manufactured by depositing a first layer 702 of reagent 206 onto a substrate 704. A second layer 706, of reagent 204, is deposited upon first layer 702. Likewise, a third layer 708 of a third reagent 202 is deposited onto second layer 706.

As each of the layers 702, 706 and 708 is deposited directly upon the other and without intervening processing steps, such as but not limited to masking, etching, and planarizing, the interfaces between each of the layers 702, 706 and 708 may be of high quality. Typically, when one material layer is deposited upon another the crystal structure of the base layer will seed the development of a crystal structure within the deposited layer. The propagation of a desirable crystal structure is often desired to establish high quality interfaces, and ultimately the operational characteristics of sensor array 700.

In addition, as the layers 702, 706, and 708 are deposited directly upon the clean substrate 201, very precise and uncontaminated amounts of the reagents may be provided. Moreover, where cells are first processed and reagents subsequently deposited therein, debris, surface tension, cell defects, and/or other factors may significantly reduce the accuracy and purity of the deposited reagents. Such issues are advantageously avoided by establishing the reagents first, and then establishing accessing apertures.

Moreover, the deposition of all layers 702, 706 and 708 prior to further processing may advantageously permit the formation of a sensors with highly uniform and/or superior operational properties.

Continuing with FIG. 7(a), a 3D patterned resist layer 710, which may be a polymer based material, is formed atop the stack of layers 702, 706, 708. As shown, 3D patterned resist layer 710 includes varying vertical heights, of which vertical heights 712 and 714 are exemplary. It can be appreciated by those skilled in the art that the number, height, and location of vertical heights 712, 714 is dependent upon the desired design of sensor array 700 in its operational state, as well as the method of etching selected and the materials used.

After a first etching step, which removes a first layer of all materials exposed to the etching process, sidewalls of reagent 202 in layer 708, e.g. sidewalls 716 and 718, are exposed (see FIG. 7(b)), as is a top surface 719 of reagent 202. Further, top surfaces 720 and 722 of reagent 204 in layer 706 are exposed as well. Also, the vertical protrusions 712, 714 of polymer material have been reduced in height.

In a subsequent etching step, the results of which are depicted in FIG. 7(c), additional polymer material from 3D patterned resist layer 710, reagent 204 from layer 706, and reagent 202 from layer 708 are removed. As a result of this etching step, sidewalls and top surfaces of reagent 204, e.g. sidewalls 724 and 726 and top surface 728, are exposed. Also, top surface 730 and 732 of reagent 206, layer 702, are revealed.

In at least one embodiment, the structure of an aperture presenting access to one or more reagents may be considered as a well or bore. It is of course understood and appreciated that the reagents constitute at least a portion of the sensor well structure as oppose to simply being deposited within a pre-existing bore. It is further understood and appreciated that the physical distance between the established bores is such that reagents within one will not inadvertently interferer with or otherwise contaminate the reactions of another, even though reagent material itself is utilized as sidewall and/or bottom material for each bore.

The final etching step establishes the structure of sensor array 700. As can be appreciated by referring to FIG. 7(d), the sensor array 700 includes: bore 734 presenting reagents 202, 204 and 206; bore 736 presenting reagents 202 and 204; and bore 738 presenting 204 and 206.

It can be appreciated that the array depicted in FIG. 7(d) is a multiple functionality sensor array 700. Multiple functionality sensor array 700 may be used to detect multiple agents (biological or otherwise) either in a single bore 732 having multiple reagents 202-206 exposed, or in multiple bore 732-736 having various combinations of reagents 202-206. Of note, bores 732-736 may or may not be co-planar with respect to a bottom surface exposed beneath the aperture and the reagent contained therein, e.g. bottom surfaces 740 and 742. In at least one embodiment, it is not required that bottom surfaces 740, 742 beneath an aperture be co-planar, as material test conditions do not require that level of control or structure uniformity.

Figure 8:
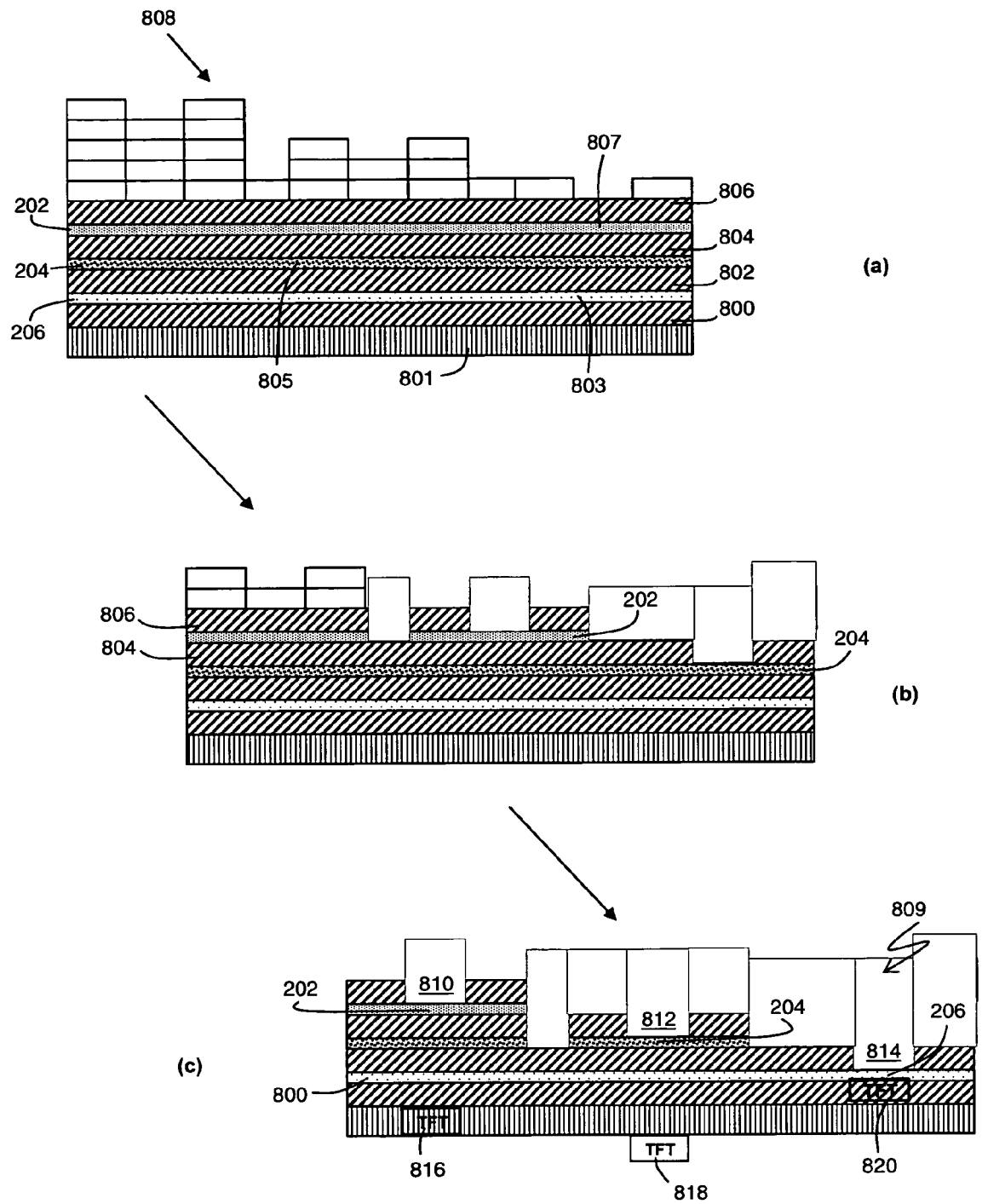
FIG. 8 is a series of side views depicting the forming of a sensor array with TFTs, according to an embodiment.
Figure 9:
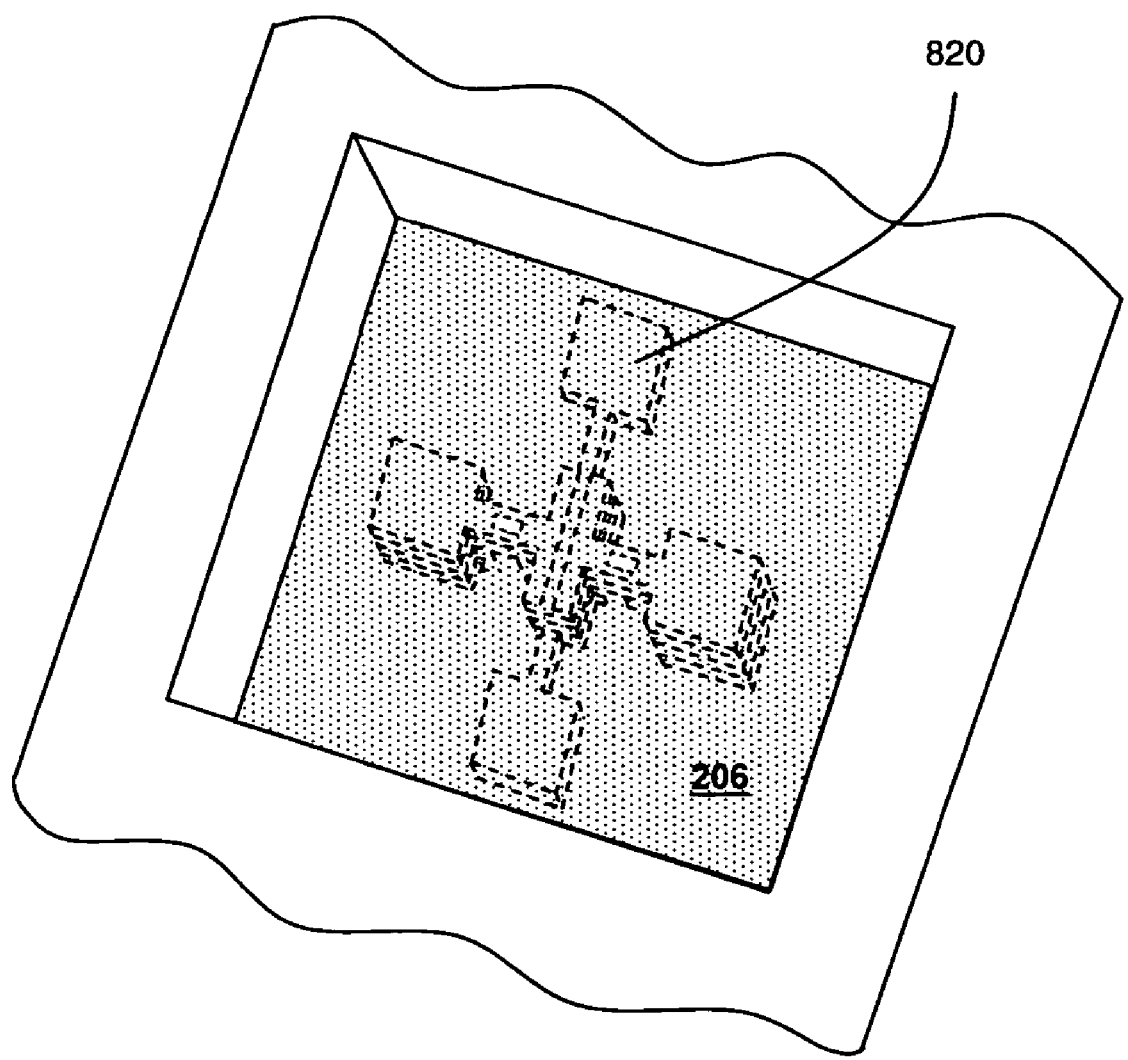
FIG. 9 is a perspective view of a TFT below a reagent material, according to an embodiment.

In at least one embodiment, reagents 202-206 must be kept separate from each other within the structure of a sensor array. As shown in FIG. 8, additional spacer material may be required to separate reagents 202-206. More specifically, in FIG. 8(a) a spacer 800 is positioned between a substrate 801 and a layer 803 of reagent 206. A second spacer 802 separates layer 803 from a layer 805 of reagent 204. Yet a third spacer 804 is required to separate layer 805 from a layer 807 of reagent 202, and a fourth spacer 806 separates layer 807 from 3D patterned resist layer 808. The spacers 800, 802, 804 and 806 may be the same material as 3D patterned resist layer 808, or they may be an alternate reactive material well known in the arts as suitable for use with the etching techniques describe herein.

After three etches of the structure depicted in FIG. 8(a), areas of spacers 804 and 806 are exposed, as are areas of reagent 202 and reagent 204 (FIG. 8(b)). Subsequent etches reveal the finished structure of a sensor array 809. As shown in FIG. 8(c), discrete exposed areas of reagents 202-206 are separated, thereby preventing the mixing of reagents 202-206. For example, bore 810 which presents reagent 202 is separate from other bores presenting the same or different reagents. Likewise, bores 812 and 814, presenting reagents 204 and 206 respectively, are each separated from any other bores.

In the operation of sensor array 809, reagents 202-206 are located below the outer surface of the sensor, though provided for use through a plurality of bores 810-814. Agents of interest, or suspected agents of interest, are introduced into bores 810-814 by any of number of techniques well known in the art. Once introduced, the agents or suspected agents interact with the one or more layers or reagent material presented below the aperture.

If the proper agent-reagent combination is achieved in a given bore, a chemical reaction will ensue. The chemical reaction may be detected using a variety of detection techniques, to include: optical detection (e.g. a change in color); thermal detection (e.g. a change in thermal emissions or reflections); or detection of an electrical current generated as a by-product of the chemical reaction.

In at least one embodiment of sensor array 809, a thin-film device may be used to detect the electrical response to the chemical interaction between agents and reagents. The thin-film device may be a rectifying device such as a diode, a junction, or a thin-film transistor or "TFT". Alternatively, the thin-film device may be a micro-electromechanical device. The manufacture of such thin-film devices, for example, is disclosed in co-pending and commonly owned U.S. patent applications Ser. No. 11/025,750, filed on Dec. 22, 2004, entitled "Method of Forming at Least One Thin Film Device," herein incorporated by reference, and U.S. patent application Ser. No.: 11/037,887, filed on Jan. 18, 2005, entitled "Thin Film Device Active Matrix by Pattern Reversal Process. " herein incorporated by reference.

The fabrication of TFTs may be an integral step in the fabrication process for sensor array 809. In particular, as the etching process proceeds to define the elements (apertures, openings, wells, bores, etc.) of sensor array 809, TFTs are manufactured as well. In this instance the "sandwich construction" of spacers, reagents, patterned resist layer, etc., from which sensor array 809 is formed, includes the necessary thin-film device layers required to form TFTs. More specifically, thin-film device layers (not shown) are deposited upon substrate 801, and 3D patterned resist layer 808 is formed over the thin-film device layers, as well as the layers of reagents 202-206.

In at least one embodiment, etching of both 3D patterned resist layer 808 and the thin-film device layers, which may include undercutting at least one thin-film device layer, produces the desired TFT. Alternatively, TFTs may be formed in a separate SAIL process and integrated into the structure of sensor array 809 in a latter manufacturing step. In at least one embodiment, the TFT device is substantially smaller than the bore areas of sensor 809 exposing the reagent materials. More specifically, in at least one embodiment, alignment of the exposed areas of reagents beneath an apertures to the TFT devices is generally not problematic, as the reagents areas are significantly larger than the TFT devices.

In FIG. 8, three TFTs 816, 818 and 820 are shown in phantom positioned within the structure of sensor array 809. In one embodiment, TFTs (e.g. TFT 816) are positioned within substrate 801, beneath the "bottom-most" spacer 800 when such spacers are used. Alternatively, TFTs may be positioned beneath substrate 801, e.g. TFT 818. In yet another embodiment, as shown in both FIG. 8 and FIG. 9, TFT 820 may be located directly beneath a layer of reagent, e.g.

reagent 206. In at least one embodiment, TFTs 816-820 may be aligned to form an active matrix backplane for sensor array 809.

Regardless of the positioning of the TFTs 816-820, the thickness of the layer or layers (nominally on the order of a few μms) between the TFTs 816-820 and the chemical reaction between agents/reagents is calculable and generally considered inconsequential. As can be appreciated by those skilled in the art, an electrical signal generated by the chemical reaction in a given location will be discernable by the TFTs 816-820, and the thickness of intervening layers can be used in calculating the actual magnitude of the electrical signal.

Changes may be made in the above methods, systems and structures without departing from the scope thereof. It should thus be noted that the matter contained in the above description and/or shown in the accompanying drawings should be interpreted as illustrative and not in a limiting sense. The following claims address all generic and specific features described herein, as well as all statements of the scope of the present method, system and structure, which, as a matter of language, might be said to fall therebetween.

What is claimed is:

1. A method of forming a sensor array comprising:
   providing a substrate;
   disposing one or more reagents upon the substrate;
   depositing at least one resist layer over the one or more reagents;
   establishing a three-dimensional masking structure in the resist layer having a plurality of different vertical heights; and
   etching the three-dimensional structure to expose portions of the one or more reagents in a plurality of separated apertures.

2. The method of claim 1, wherein the substrate is flexible.

3. The method of claim 1, wherein the etching is an anisotropic etch.

4. The method of claim 1 which includes self-aligning, imprint lithography.

5. The method of claim 1 further comprising imprinting a single polymer resist layer with a three-dimensional template to establish patterning and alignment of the three-dimensional structure for etching.

6. The method of claim 1, wherein the one or more reagents are biological reagents.

7. The method of claim 1, wherein a plurality of different reagents are deposited on the substrate according to a predetermined pattern, at least a portion of the pattern exposed in one or more apertures.

8. The method of claim 1, wherein a concentration of a given reagent on the substrate varies according to a predetermined pattern, the concentration of the given reagent exposed in at least one aperture being different from the concentration of the same given reagent exposed in at least one other aperture.

9. The method of claim 1, wherein the sensor array is in electrical contact with at least one thin-film device.

10. The method of claim 9, wherein forming the thin-film device comprises:
    providing a substrate;
    depositing a plurality of thin-film device layers upon the substrate;
    providing an imprinted three-dimensional masking structure upon the plurality of thin film device layers;
    etching the three-dimensional structure and plurality of thin-film device layers; and undercutting at least one thin-film device layer.

11. The method of claim 9, wherein the thin-film device is a rectifying device selected from the group consisting of a diode, a junction or a transistor.

12. The method of claim 9, wherein the thin-film device is a micro-electromechanical device.

13. The method of claim 9 further comprising providing a plurality of thin-film devices to form an active matrix backplane.

14. A method of testing for one or more chemical reactions using an active sensor array comprising:
    providing a substrate in electrical contact with one or more thin-film devices;
    disposing one or more reagents upon the substrate;
    depositing a resist layer over the one or more reagents;
    establishing a three-dimensional masking structure in the resist layer having a plurality of different vertical heights;
    etching the three-dimensional structure to create a plurality of separated apertures exposing portions of the one or more reagents;
    introducing a test material into the plurality of apertures; and
    detecting and measuring at least one electrical output generated by a chemical reaction between the one or more reagents and the test material.

15. The method of claim 14, wherein the test material includes a plurality of substances detectable by the one or more reagents.

16. The method of claim 14, wherein the thin-film device is a rectifying device selected from the group consisting of: a diode, a junction or a transistor.

* * * * *